United States Patent
Gill et al.

(10) Patent No.: US 10,105,438 B2
(45) Date of Patent: Oct. 23, 2018

(54) PROCESS OF CONJUGATION AND NOVEL SYNTHETIC OLIGOSACCHARIDE-PROTEIN CONJUGATES OBTAINED THEREOF

(71) Applicant: MSD WELLCOME TRUST HILLEMAN LABORATORIES PVT. LTD., New Delhi (IN)

(72) Inventors: Davinder Gill, New Delhi (IN); Manoj Kumar Chhikara, Delhi (IN); Rakesh Rana, New Delhi (IN); Juned Dalal, New Delhi (IN); Deepti Singh, New Delhi (IN)

(73) Assignee: MSD WELLCOME TRUST HILLEMAN LABORATORIES PVT. LTD., New Delhi (IN)

( * ) Notice: Subject to any disclaimer, the term of this patent is extended or adjusted under 35 U.S.C. 154(b) by 0 days.

(21) Appl. No.: 15/516,445

(22) PCT Filed: Oct. 8, 2015

(86) PCT No.: PCT/IB2015/057682
§ 371 (c)(1),
(2) Date: Apr. 3, 2017

(87) PCT Pub. No.: WO2016/055957
PCT Pub. Date: Apr. 14, 2016

(65) Prior Publication Data
US 2017/0246313 A1  Aug. 31, 2017

(30) Foreign Application Priority Data
Oct. 9, 2014 (IN) .......................... 2884/DEL/2014

(51) Int. Cl.
| | | |
|---|---|---|
| *G01N 33/554* | (2006.01) |
| *G01N 33/569* | (2006.01) |
| *A61K 39/385* | (2006.01) |
| *C07H 3/06* | (2006.01) |
| *C07K 14/33* | (2006.01) |
| *C07K 14/34* | (2006.01) |
| *C08B 37/00* | (2006.01) |
| *C08H 1/00* | (2006.01) |
| *A61K 39/095* | (2006.01) |
| *A61K 39/102* | (2006.01) |
| *A61K 47/64* | (2017.01) |
| *A61K 39/00* | (2006.01) |

(52) U.S. Cl.
CPC .......... *A61K 39/385* (2013.01); *A61K 39/095* (2013.01); *A61K 39/102* (2013.01); *A61K 47/646* (2017.08); *A61K 47/6415* (2017.08); *C07H 3/06* (2013.01); *C07K 14/33* (2013.01); *C07K 14/34* (2013.01); *C08B 37/00* (2013.01); *C08H 1/00* (2013.01); *A61K 2039/575* (2013.01); *A61K 2039/6037* (2013.01)

(58) Field of Classification Search
None
See application file for complete search history.

(56) References Cited

FOREIGN PATENT DOCUMENTS

WO  2005/003775 A2  1/2005

OTHER PUBLICATIONS

Wright et al., "Preparation of synthetic glycoconjugates as potential vaccines against Shigella flexneri serotype 2a disease", Organic Biomolecular Chemistry, 2004, pp. 1518-1527, vol. 2.
Belot et al., "Synthesis of two linear PADRE conjugates bearing a deca-or pentadecasaccharide B epitope as potential synthetic vaccines against Shigella flexneri serotype 2a infection", Chemistry—A European Journal, 2005, pp. 1625-1635, vol. 11.

*Primary Examiner* — Gary B Nickol
*Assistant Examiner* — Khatol S Shahnan Shah
(74) *Attorney, Agent, or Firm* — W&C IP

(57) ABSTRACT

The present invention relates to an improved process of conjugation to obtain synthetic oligosaccharide-protein (OS-PR) conjugates. The process of synthetic OS-PR conjugation is a rapid process providing oligosaccharide-protein conjugates which are highly immunogenic and elicit specific and homogenous immune responses. The synthetic oligosaccharide comprising of four to eight repeating units of respective monomers and at least one in-built terminal amino linker, said synthetic polysaccharide mimics natural polysaccharide obtained from gram negative bacteria such as *Neisseria meningitidis* serogroups A, C, Y, W, X and *Haemophilus influenzae* and carrier protein is obtained from gram positive bacteria such as *Clostridium tetani* (tetanus toxoid) or *Corynebacterium diphtheriae* (CRM197) or their recombinant versions. The conjugation chemistry of the said oligosaccharide-protein conjugate of the present invention is thio-ether linkage. The present invention takes complete process time in the range of 14-22 hours. The said oligosaccharide-protein conjugates are useful in production of monovalent vaccine or multivalent combination vaccines and as diagnostic tool.

21 Claims, 8 Drawing Sheets

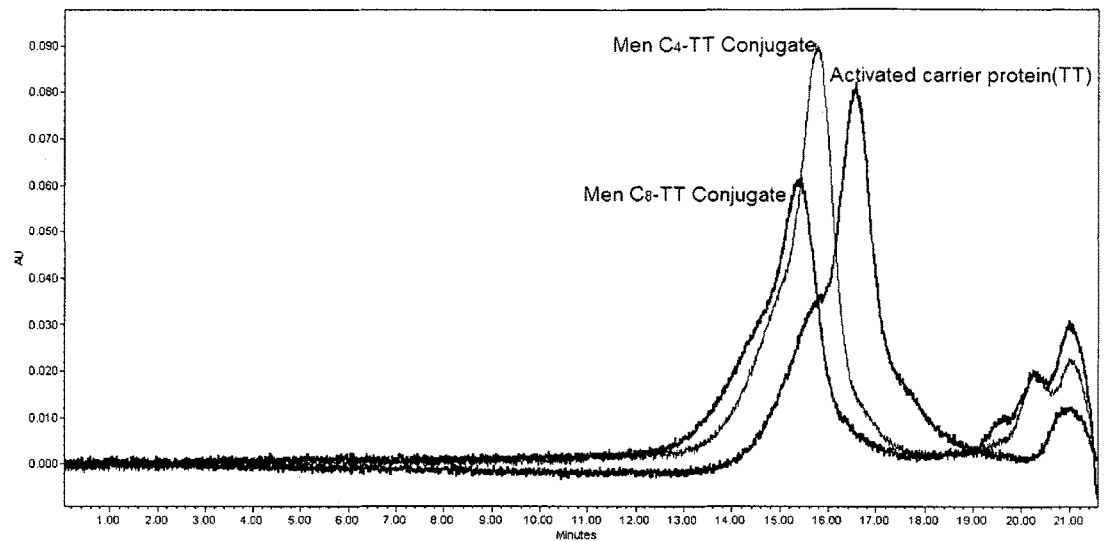
Figure 3a
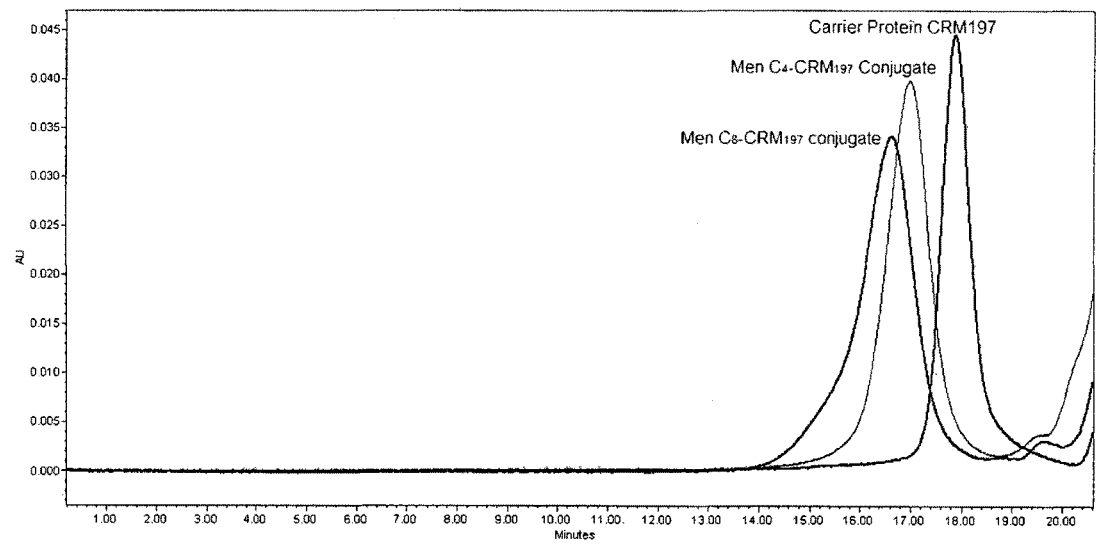
-Figure 3b

PROCESS OF CONJUGATION AND NOVEL SYNTHETIC OLIGOSACCHARIDE-PROTEIN CONJUGATES OBTAINED THEREOF

FIELD OF INVENTION

The present invention relates to an improved process of conjugation to obtain novel synthetic oligosaccharide-protein (OS-PR) conjugates. The present invention also relates to novel synthetic OS-PR conjugates for the preparation of novel conjugate vaccines wherein said oligosaccharides are synthetic oligosaccharides.

BACKGROUND OF THE INVENTION

Oligosaccharides which correspond to small fraction of natural bacterial capsular polysaccharides are recognized by antibodies raised against high molecular weight native polysaccharide antigens. The oligosaccharides give promising possibilities as lead vaccine candidates as they are not only immunogenic, but can also function as haptens in their protein conjugates that can elicit specific antibodies in animal models and in humans. Advances in the field of biological research and new generation organic synthetic vaccine technology have provided more effective chemical assembly of the complex oligosaccharide fragments in organic synthetic lab which are generally available on and are purified from the surface of pathogenic bacteria.

The conjugates obtained from natural polysaccharides have been successfully developed as human vaccines. However, their use is associated with problems such as significant variation in size and properties of bacterial polysaccharides, the destruction of vital immuno-dominant features during the chemical conjugation to a carrier protein, display of significant heterogeneity in conjugates and presence of highly toxic components and other host cell impurities that may be difficult to remove. Organic synthesis can provide carbohydrate epitopes in high purity and in relatively large amounts for controlled conjugation to a carrier protein. In such an approach, synthetic saccharides are equipped with an artificial spacer to facilitate selective conjugation to a carrier protein.

The advent of conjugate vaccines against *Haemophilus influenzae* type b-associated diseases have opened a new era in vaccinology. One of the major milestones in the development of new generation vaccines is the development of efficacious protein conjugates of synthetic fragments of the capsular oligosaccharide of *Haemophilus influenzae* type b in preventing childhood meningitis and other diseases. The key issues pertaining to the development of synthetic oligosaccharide and their conjugates are manifold such as epitope size, the number of oligosaccharide copies per protein in the conjugate, the possible effect of the spacer on immune response, and the proper choice of the carrier protein combined with the selection of the animal model.

Given the fact that the synthetic oligosaccharide provides the effective lead compounds for the biological research, specifically in the field of vaccine technology, the significant research is going on for the preparation of the synthetic oligosaccharides and their protein conjugates. However, there is no general protocol for the preparation of the oligosaccharide of the biological importance. The chemical synthesis of each lead conjugate molecule is a research project which takes long and systematic experimentation. The total process time documented in the prior art from raw material to the product takes 20-24 hours. The lower yield, less stability and less purity of the conventional oligosaccharide and their protein conjugate are the main issues of concern. Therefore, there is an urgent long felt need to have synthetic oligosaccharide-protein conjugates with higher stability coupled with homogeneity and an efficient synthetic OS-PR conjugation process to obtain such synthetic conjugate vaccines with better yield, stability and purity. The affordability and availability of the synthetic conjugate vaccines is a significant problem which requires a process that enables the availability of synthetic conjugate vaccines in a time-effective and cost-effective manner.

OBJECT OF THE INVENTION

In order to obviate the drawbacks in the existing state of art, the main object of present invention is to provide an improved process of conjugation to obtain novel synthetic oligosaccharide-protein (OS-PR) conjugates.

Another object of present invention is to provide an improved process of synthetic OS-PR conjugation wherein said process enables for higher yield, higher purity and higher stability of oligosaccharide-protein conjugates.

Yet another object of present invention is to provide an improved process of synthetic OS-PR conjugation wherein said process is rapid and convenient for the conjugation of said oligosaccharide and carrier protein.

Yet another object of present invention is to provide a cost effective improved process of synthetic OS-PR conjugation to obtain affordable oligosaccharide-protein conjugates.

Yet another object of the present invention is to provide novel synthetic OS-PR conjugates for the preparation of novel conjugate vaccines.

Yet another object of present invention is to provide novel synthetic OS-PR conjugates wherein the oligosaccharides are synthetic oligosaccharides.

Yet another object of present invention is to provide synthetic OS-PR conjugates wherein said oligosaccharide-protein conjugates elicit specific and homogenous immune response.

Yet another object of present invention is to provide novel synthetic OS-PR conjugates for the preparation of novel synthetic oligosaccharide based conjugates used either as monovalent or as combination vaccines, and also as diagnostic tools.

SUMMARY OF THE INVENTION

Accordingly, the present invention provides an improved process of conjugation to obtain novel synthetic OS-PR conjugates. The process of synthetic OS-PR conjugation of present invention is a rapid process providing OS-PR conjugates which elicit high, monospecific and homogenous immune responses. The conjugates thus produced give reproducible results which enhance the reliability of the vaccines and diagnostics based on these conjugates.

The novel synthetic OS-PR conjugates obtained from the process of present invention yields novel synthetic oligosaccharide based conjugate vaccines.

Said synthetic conjugates are synthetic in that the oligosaccharide part of the synthetic OS-PR conjugates is a synthetic oligosaccharide, whereas the carrier protein is obtained from gram positive bacteria.

The present invention involves the selection of a suitable lengths of synthetic oligosaccharide, preferably oligosaccharide tetramer and octamer (hereinafter oligomer), which is modified for the conjugation with the protein. The modification comprises the steps of addition of a linker to that oligomer, activation of said oligomer using thiolating agent followed by purification of said activated oligomer (that is thiolated oligomer). On the other hand, a suitable bacterial protein, preferably but not limited to tetanus toxoid, is modified by activation. The said thiolated oligomer is conjugated with said activated bacterial protein.

The linker in-built into the said oligomer provides amino group (—NH2) at the terminal end of the said oligomer. The said terminal amino group (—NH2) is easily available for activation with the thiolating agent. The thiolating agent is selected from a group of reagents such as, but not limited to thioacetic acid and N-Succinimidyl S-Acetylthioacetate (SATA), preferably SATA. The resultant sulfhydrilated compound is then treated with nucleophile selected from the group of reducing agents to obtain activated oligomer which is then purified. The assay is carried out to ascertain the thiol units per oligosaccharide units.

The said protein is activated using a crosslinker such as N-(beta-Maleimidopropyloxy) succinimide ester (BMPS). Said activated oligosaccharide and said activated protein are kept at certain experimental conditions such as at specific temperature for specific time for conjugation.

The conjugation chemistry of the said oligosaccharide-protein conjugate of the present invention is thio-ether linkage.

The present invention provides the synthetic conjugation in which the complete process time is in the range of 14-22 hours. The present invention does not require nitrogen purging and uses the reagents for which no specific handling skills are required, thereby making the process convenient and cost effective.

The present invention provides the conjugates without any modification of the parent oligomeric backbone, thus keeping all the epitopes intact to generate natural immune response.

The oligosaccharide and protein ratio has a critical role in the generation of immune response. The present invention provides to get a higher oligosaccharide loading on protein to get a desired OS:PR ratio between 0.2 to 0.5 for *Haemophilus influenzae* type b (Hib) and *Neisseria meningitidis* serogroups A, C, Y, W135 or X (MenA, MenC, MenY, MenW or MenX, respectively). The overall conjugation yield of the oligosaccharide protein conjugate is about 45% to 65% for Hib and 21% to 48% for MenA/C/Y/W/X serogroups. The present invention also uses N-Succinimidyl S-Acetylthioacetate (SATA) for the activation of oligomer. SATA is soluble in dimethyl sulphoxide (DMSO) and enables rapid mixing of oligosaccharide with the thiolating agent in buffer, thereby easing the process. The present invention also provides the process of synthetic conjugation wherein single step purification is carried out, thereby reducing the steps in the process, resulting into better yield and lesser process time.

The improved process of the present invention is useful for the preparation of a number of conjugates useful in the preparation of vaccines. A few non-limiting examples of such OS-TT conjugates are Hib-TT Conjugate, MenX-TT conjugate, MenC-TT conjugate, MenA-TT conjugate, MenW-TT conjugate, MenY-TT conjugate, Hib-CRM197 conjugate, MenX-CRM197 conjugate, MenC-CRM197 conjugate, MenA-CRM197 conjugate, MenW-CRM197 conjugate, MenY-CRM197 conjugate. The vaccine can be prepared either as single or as combination vaccines.

Out of the many examples in which the process of synthetic OS-PR conjugation can be used, in one non-limiting example, the said synthetically prepared oligomer is linked with hexaylamine linker and activated using (N-Succinimidyl S-Acetylthioacetate (SATA), wherein said SATA is dissolved in dimethyl sulphoxide (DMSO). The sulfhydrilated oligosaccharide thus obtained is subjected to predetermined conditions for a fixed period at a very low flow rate and then purified. The said purified oligomer is then concentrated and reacted with at least one nucleophile such as Hydroxyl amine hydrochloride to obtain thiolated oligosaccharide.

A solution of N-(β-Maleimidopropyloxy) succinimide ester in N-Methyl-2-Pyrrolidone (NMP) is mixed with a carrier protein e.g. tetanus toxoid (TT) (obtained from *Clostridium tetani*) or CRM197 (cross reacting mutant or non-toxic mutant of diphtheria toxin and also referred to as CRM in the specification) and kept in predetermined conditions for fixed period. The reaction mixture of said activated carrier protein is then purified and collected.

The esterified or activated carrier protein and said thiolated oligomer are mixed and incubated overnight at predetermined conditions. The oligomer-protein conjugate bulk is purified using ultracentrifugal filters or other size exclusion devices e.g. gel filtration chromatography.

The most significant outcome of the improved process of present invention is to provide oligosaccharide-protein conjugates such as but not limited to MenA-TT, MenC-TT, MenX-TT, MenY-TT, MenW-TT, Hib-TT conjugate from synthetic OS-PR conjugation with reproducible results. The said oligosaccharide-protein conjugate elicit specific and homogenous immune response and is useful as production of monovalent vaccine or multivalent combination vaccines and as diagnostic tool.

BRIEF DESCRIPTION OF DRAWINGS

FIG. 1 collectively depicts diagrammatic representation of structures of synthetic oligomers of different Meningococcal serogroups.

FIGS. 3a and 3b depicts HP-SEC peak profile of conjugated oligomer (MenC)$_4$ or (MenC)$_8$ compared to the activated protein (TT & CRM), as observed on Waters UV/PDA detector.

DETAILED DESCRIPTION OF THE INVENTION WITH ILLUSTRATIONS AND EXAMPLES

Accordingly the present invention provides an improved process of conjugation for the preparation of synthetic oligosaccharide-protein conjugates useful in the preparation of vaccines.

A few non-limiting examples of such conjugates are Hib-TT Conjugate, MenX-TT conjugate, MenC-TT conjugate, MenA-TT conjugate, MenW-TT conjugate, MenY-TT conjugate, Hib-CRM197 conjugate, MenX-CRM197 conjugate, MenC-CRM197 conjugate, MenA-CRM197 conjugate, MenW-CRM197 conjugate, MenY-CRM197 conjugate. The vaccine can be prepared either as monovalent or as combination vaccines.

Figure 1A:
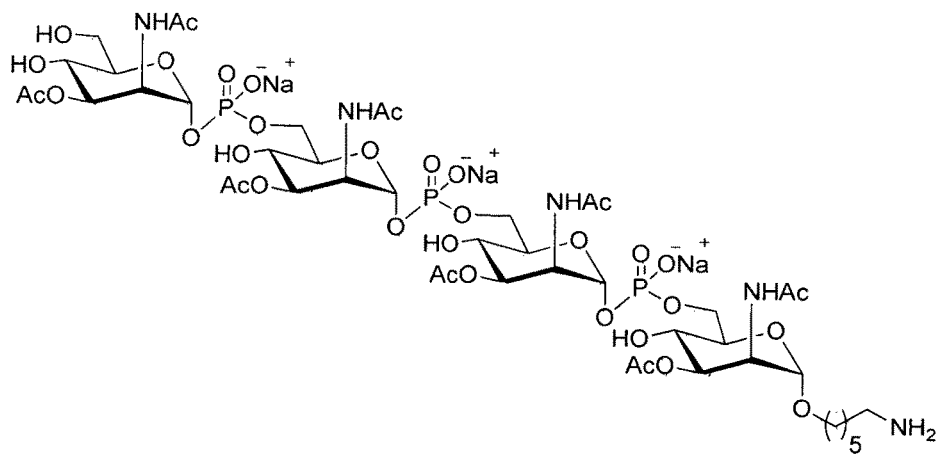
FIG. 1a: MenA.
Figure 1B:
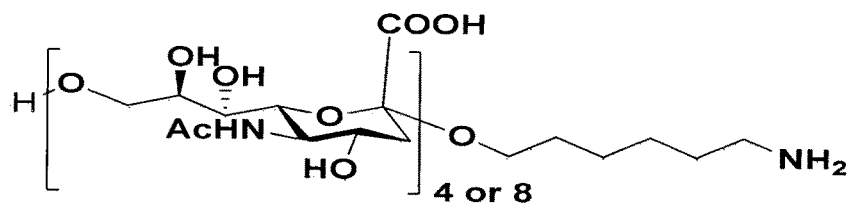
FIG. 1b: MenC.
Figure 1C:
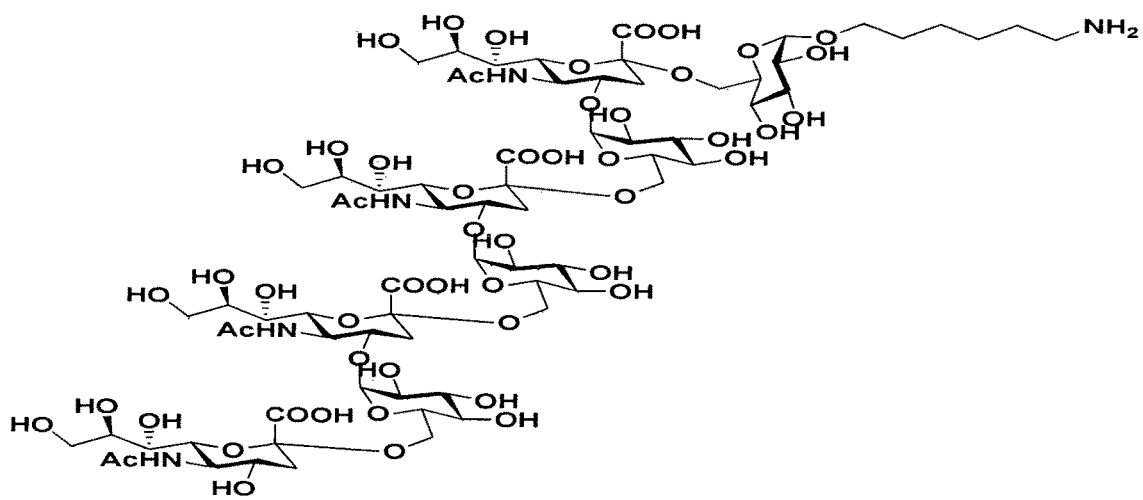
FIG. 1c: MenY.
Figure 1D:
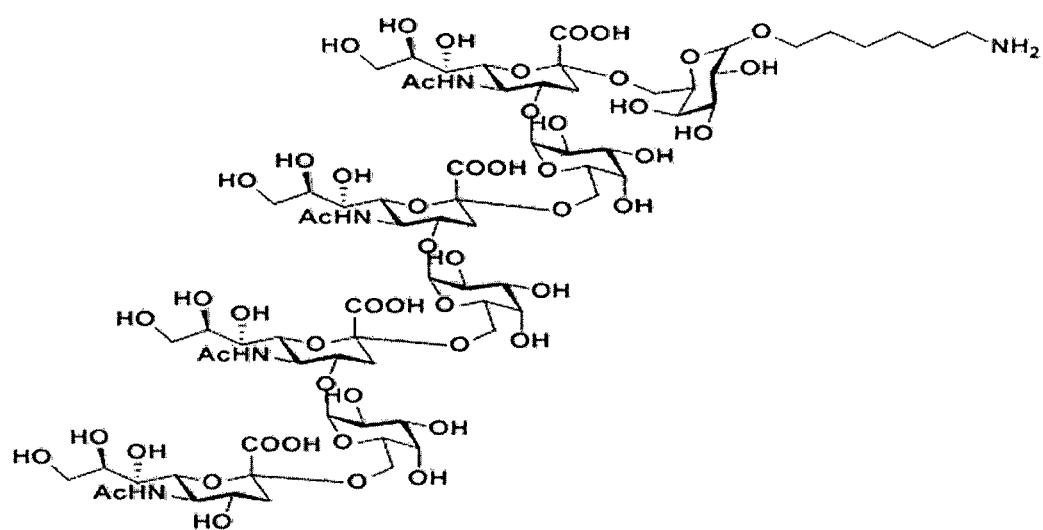
FIG. 1d: MenW$_{135}$
Figure 1E:
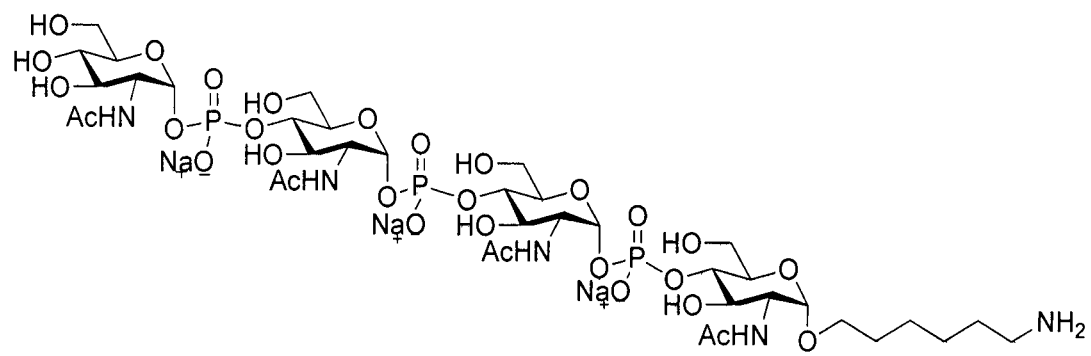
FIG. 1e: MenX with terminal amine containing linker.
Figure 2A:
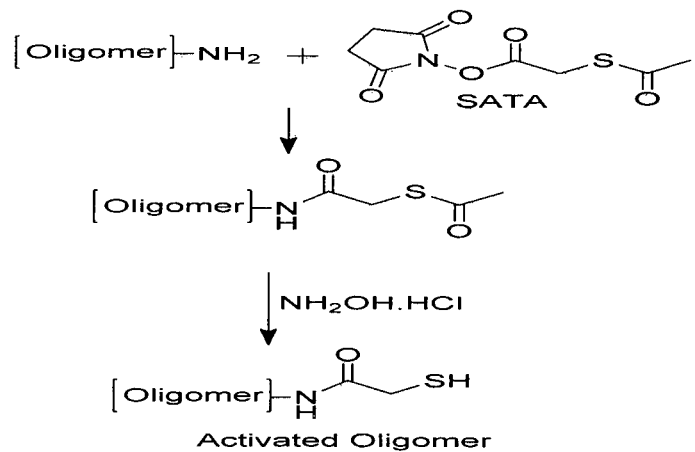
FIG. 2a depicts diagrammatic representation of the process of activation of oligomers to generate the reactive terminal thiol group.

The present invention involves the selection of a suitable synthetic oligomer, preferably oligosaccharide tetramer and octamer, the synthetic oligosaccharide comprising of at least one in-built terminal amino linker, the said synthetic oligosaccharide mimics natural polysaccharide obtained from gram negative bacteria such as *Neisseria meningitidis* serogroup A, C, Y, W135, X (FIG. 1a, 1b, 1c, 1d, 1e) and *Haemophilus influenzae* with terminal amino linker (—NH2). The said terminal amino group (—NH2) is easily available for activation with the sulfhydrylating agent. The sulfhydrylating agent which facilitate conversion of terminal amino linker to sulfhydryl group, is selected from a group of reagents such as, but not limited to, acetic anhydride, acetyl chloride, N-acetylhomocysteine thiolactone, homocysteine thiolactone, thioacetic acid and N-Succinimidyl S-Acetylthioacetate (SATA), preferably SATA. SATA is dissolved in dimethylsulfoxide (DMSO) and stirred with the solution of said synthetic oligosaccharide for 1 hour at room temperature. The reaction mixture is then applied to gel filtration chromatography, equilibrated with HEPES buffer ~pH 7.5 to remove any unreacted SATA. The said SATA modified oligomer is then mixed at room temperature for 2 hour with nucleophile selected from a group of reducing agents, preferably hydroxyl amine hydrochloride to facilitate conversion of sulfhydryl group to reactive thiol group (FIG. 2a). The determination of oligosaccharide content is carried out for Men C, Y and W by Resorcinol assay, for Men X and A by Chen's assay and for Hib by Orcinol assay. Thiol (—SH) content is determined by Ellman assay for all the types of Oligomers. Extent (%) of thiolation is determined by dividing concentration of thiol by concentration of oligomer on a molar basis.

Figure 2B:
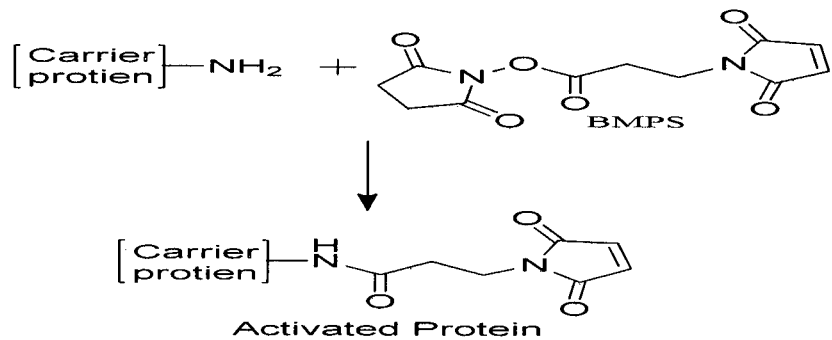
FIG. 2b depicts schematic diagram showing the activation of carrier protein to generate the maleimide group reactive towards thiols.

A suitable bacterial carrier protein, preferably but not limited to tetanus toxoid (TT) and cross reacting mutant (CRM197 or simply CRM) or their recombinant version is activated to generate the reactive maleimide functional group. The said carrier protein is activated using an aliphatic heterobifunctional crosslinker preferably but not limited to N-(beta-Maleimidopropyloxy) succinimide ester (BMPS). The said carrier protein e.g. TT and CRM197 in HEPES buffer ~pH 7.6 and mixed at room temperature with said solution of BMPS in N-Methyl-2-Pyrrolidone (NMP) for 2 hour. The reaction mixture of said carrier protein is then washed 6-7 times with PBS buffer ~pH 6.8 through suitable centrifugal cutoff filters (FIG. 2b). The protein content of said activated carrier protein is determined by Lowry method using BSA as standard. The maleimide content is estimated indirectly by Ellman assay, where maleimide labelled carrier protein is first reacted with known amount β-mercaptoethanol and unreacted β-mercaptoethanol is analyzed by DTNB. The number of maleimide groups per unit of carrier protein is calculated using Molar concentration of carrier protein and Molar concentration of maleimide.

Figure 2C:
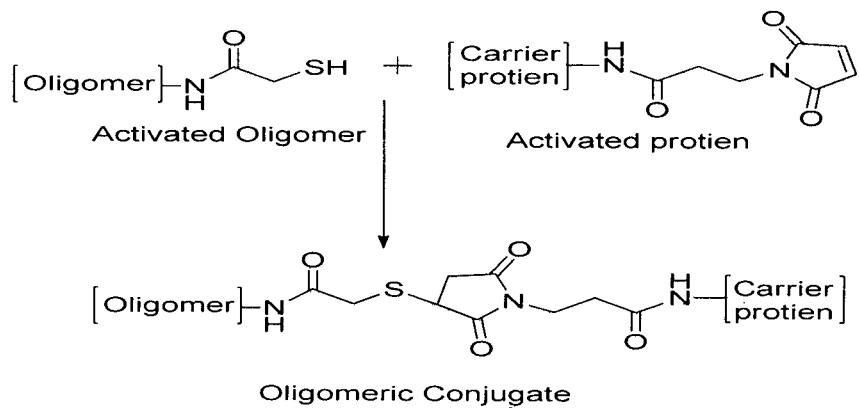
FIG. 2c depicts schematic diagram showing the conjugation of thiolated synthetic oligomer to maleimide labelled carrier protein via thio-ether linkage.

The thiolated oligosaccharide selected from the group of gram negative bacteria such as *Neisseria meningitidis* serogroup A, C, Y, W135, X and *Haemophilus influenzae* type b in HEPES buffer ~pH 7.5 and said activated carrier protein labeled with maleimide selected from tetanus toxoid (TT) and cross reacting mutant (CRM197) in PBS buffer ~pH 6.8 are mixed together for conjugation. The reaction mixture having pH in the range of 6.5 to 7.5 is stirred gently overnight preferably at 2-8° C., though this can be carried out at room temperature. The crude conjugate is purified by washing 6-7 times with MES buffer ~pH 6.5 through 50 kD cutoff centrifugal filters to remove unconjugated oligomer and impurities like unreacted hydroxylamine hydrochloride. The final purified oligosaccharide-protein conjugates are filtered through 0.2 μ filters and stored at 2-8° C. till use (FIG. 2c). The conjugation chemistry of the said oligosaccharide-protein conjugate of the present invention is thioether linkage.

The oligosaccharide-protein conjugates obtained from said improved conjugation process are further characterized for physicochemical analysis such as protein content, oligosaccharide content, oligosaccharide protein ratio, the free oligosaccharide content by standard methods. The conjugates are analyzed by high performance size exclusion chromatography (HP-SEC) to observe the conversion of reactants into conjugate and molecular size distribution (FIG. 3a, 3b, 3c, 3d). Studies for testing antigenicity (FIG. 4) and animal immunogenicity of the oligosaccharide-protein conjugates thus obtained are conducted (FIG. 5a, 5b, 5c, 5d).

The present invention provides the synthetic conjugation in which the complete process time is in the range of 14-22 hours. The present invention does not require nitrogen purging and uses the reagents for which no specific handling skills are required, thereby making the process convenient and cost effective.

The present invention provides the conjugates without any modification of the parent oligomeric backbone, thus keeping all the epitopes intact to generate natural immune response. The present invention also provides the process of synthetic conjugation wherein single step purification is carried out, thereby reducing the steps in the process, resulting into better yield and lesser process time.

The most significant outcome of the improved process of present invention is to provide an oligosaccharide-protein conjugates such as but not limited to Hib-TT Conjugate, MenX-TT conjugate, MenC-TT conjugate, MenA-TT conjugate, MenW-TT conjugate, MenY-TT conjugate, Hib-CRM197 conjugate, MenX-CRM197 conjugate, MenC-CRM197 conjugate, MenA-CRM197 conjugate, MenW-CRM197 conjugate, MenY-CRM197 conjugate from synthetic OS-PR conjugation with reproducible results. The said oligosaccharide-protein conjugates elicit specific and homogenous immune response and are useful as production of monovalent vaccine or multivalent combination vaccines and as diagnostic tool.

EXAMPLE 1

Activation and Analysis of Oligomer (MenA, MenC, MenY, MenW, MenX and Hib) to Generate the Reactive Thiol Functional Group The solution of synthetic oligosaccharide at the concentration of 10 mg/ml in 0.1 M HEPES buffer containing 0.15 M NaCl, 10 mM EDTA, pH 7.5, has been mixed with solution of 2.5× molar excess of S-acetylthioglycolic acid N-hydroxysuccinimide ester (SATA) in dimethylsulfoxide. The solution has been gently stirred for 1 hour at room temperature. The SATA reacts with the amine present in the linker chain of the synthetic oligomers to form an acetylated intermediate for generation of reactive thiol groups in the second reaction step. The reaction mixture has been applied to gel filtration chromatography over sephadex G-10 (GE Healthcare) column (20-30 ml bed volume), equilibrated with 0.1 M HEPES buffer containing 0.15 M NaCl, 10 mM EDTA, pH 7.5 to remove any unreacted SATA. The reacted oligomer has been collected in 4.0 ml eluent in isocratic mode using equilibration buffer, which has been subsequently concentrated to 500 µl. The SATA-modified oligomer thus obtained has been mixed with solution of hydroxylamine hydrochloride in a concentration of about 35 molar excess of thiolated oligomer in 0.1 M HEPES buffer containing 0.15 M NaCl, 10 mM EDTA, pH 7.5. After 2 hour mixing at room temperature, the thiolated oligomer has been stored at −20° C. till further use. The schematic diagram of the activation of oligomer is shown in FIG. 2a. Two different anomers of MenX tetramer were used i.e. an alpha anomer (αXTM) and beta anomer (βXTM) for activation and conjugation.

The activated oligomer is then purified and analyzed for oligosaccharide content and thiol content.

For MenC, MenY & MenW the oligosaccharide content has been determined by Resorcinol assay using N-acetyl neuraminic acid (NANA) as a standard, for MenA and MenX by Chen's assay using phosphorus as a standard and for Hib by Orcinol assay using ribose as a standard. Thiol (SH) content has been determined by Ellman assay. The % thiolation is obtained by dividing mMolar concentration of thiols by mMolar concentration of oligomer. Few representative results of oligomer activation experiments are given in Table 1, 2, 3 and 4.

TABLE 1

Activation of MenC synthetic tetramer (MenC)$_4$ to generate reactive thiol group

| Sr. | Lot No of thiolated (MenC)$_4$ | —SH/(Hib)$_4$ (mol/mol) | % Recovery of (MenC)$_4$ (Scale of reaction) |
|---|---|---|---|
| 1 | CTM001 | 0.66 | 56 (8 mg) |
| 2 | CTM002 | 0.43 | 87 (5 mg) |
| 3 | CTM003 | 0.63 | 58 (5 mg) |
| 4 | CTM004 | 0.66 | 62 (10 mg) |
| 5 | CTM005 | 0.55 | 70 (10 mg) |
| 6 | CTM006 | 0.60 | 86 (7 mg) |
| 7 | CTM007 | 0.56 | 70 (8 mg) |
| 8 | CTM008 | 0.60 | 70 (7 mg) |
| 9 | CTM009 | 0.67 | 55 (15 mg) |
| 10 | CTM010 | 0.60 | 70 (9 mg) |

TABLE 2

Activation of MenC synthetic octamer (MenC)$_8$ to generate reactive thiol group

| Sr. | Lot No of thiolated (MenC)$_8$ | —SH(OS)$_4$ (mol/mol) | % Recovery of (MenC)$_8$ (Scale of reaction) |
|---|---|---|---|
| 1 | COM001 | 0.74 | 70 (9.5 mg) |
| 2 | COM002 | 0.72 | 69 (16 mg) |
| 3 | COM003 | 0.88 | 64 (9 mg) |
| 4 | COM004 | 0.62 | 56 (9 mg) |
| 5 | COM005 | 0.31 | 60 (18 mg) |
| 6 | COM006 | 0.43 | 40 (25 mg) |
| 7 | COM007 | 0.58 | 77 (9 mg) |
| 8 | COM008 | 0.64 | 70 (9 mg) |
| 9 | COM009 | 0.58 | 66 (9 mg) |
| 10 | COM010 | 0.68 | 49 (34 mg) |
| 11 | COM011 | 0.57 | 73 (10 mg) |

TABLE 3

Activation of MenX synthetic tetramer (MenX)$_4$ to generate reactive thiol group

| Sr. | Lot No of thiolated (MenX)$_4$ | —SH/(OS)$_4$ (mol/mol) | % Recovery of (MenX)$_4$ (Scale of reaction) |
|---|---|---|---|
| 1 | βXTM001 | 0.92 | 70 (5 mg) |
| 2 | βXTM002 | 0.72 | 65 (8.5 mg) |
| 3 | αXTM001 | 0.70 | 76 (15 mg) |
| 4 | αXTM002 | 0.54 | 83 (18.5 mg) |
| 5 | αXTM003 | 0.64 | 89 (18 mg) |

TABLE 4

Activation of Hib synthetic tetramer (Hib)$_4$ to generate reactive thiol group

| Sr | Lot No of thiolated (Hib)$_4$ | —SH/(OS)$_4$ (mol/mol) | % Recovery of (Hib)$_4$ (Scale of reaction) |
|---|---|---|---|
| 1 | HTM001 | 0.92 | 70 (5 mg) |
| 2 | HTM002 | 0.72 | 65 (8.5 mg) |
| 3 | HTM003 | 0.70 | 76 (15 mg) |
| 4 | HTM004 | 0.54 | 83 (18.5 mg) |
| 5 | HTM005 | 0.64 | 89 (18 mg) |
| 6 | HTM006 | 0.83 | 80 (10 mg) |
| 7 | HTM007 | 0.81 | 80 (10 mg) |

The process of activation of oligomer results into activated synthetic oligosaccharides with terminal amine linker. FIG. 1 collectively as FIG. 1a, 1b, 1c, 1d, 1e represents different synthetic meningococcal serogroups with terminal amine linker used for preparation of different oligomeric-protein conjugates by thioether conjugation chemistry.

EXAMPLE 2

Activation and Analysis of TT to Generate the Reactive Maleimide Functional Group Tetanus toxoid (TT) has been taken at a concentration of 20 mg/ml, (0.133mMolar) in 0.1 M HEPES buffer, pH 7.6 and is reacted with 7.2 mg of N-(beta-Maleimidopropyloxy) succinimide ester (BMPS) (27 mMolar) in 1-Methyl-2-pyrrolidinone. After 2 hour mixing at room temperature, the reaction mixture has been washed 6-7 times with 0.1 M PBS buffer containing 0.15 M NaCl, 5 mM EDTA, pH 6.8 through 50 kD cutoff centrifugal filters. Activated TT has been collected in a volume of 0.5 ml in 0.1 M PBS buffer containing 0.15 M NaCl, 5 mM EDTA, pH 6.8 and used further for the conjugation in example 4. The schematic diagram for the process of activation of TT is shown in FIG. 2b.

Activated protein is analyzed for protein content and maleimide content. Protein content of activated TT has been determined by Lowry method using BSA as a standard; and maleimide content has been estimated indirectly by Ellman assay, where maleimide labelled TT has been first reacted with known amount of β-mercaptoethanol and unreacted β-mercaptoethanol has been analyzed by DTNB. The number of maleimides per TT molecule is calculated by Molar concentration of TT and maleimide. The data for analysis of activated TT is given in Table 5.

TABLE 5

Activation of protein (Tetanus Toxoid) to generate reactive maleimide group.

| Lot no. of maleimide labelled TT | Maleimide/TT (mol/mol) | % Recovery of TT (Scale of reaction) |
|---|---|---|
| Lot 1 | 38 | 74 (10 mg) |
| Lot 2 | 41 | 95 (20 mg) |
| Lot 3 | 35 | 98 (20 mg) |
| Lot 4 | 38 | 91 (20 mg) |
| Lot 5 | 35 | 88 (20 mg) |
| Lot 6 | 39 | 80 (20 mg) |
| Lot 7 | 35 | 80 (20 mg) |
| Lot 8 | 32 | 80 (20 mg) |

EXAMPLE 3

Activation of CRM197 to Generate the Reactive Maleimide Functional Group

CRM197 has been taken at a concentration of 25 mg (0.24 mMolar) in 1.8 ml of 0.1 M HEPES buffer, pH 7.6 and reacted with 2.6 mg of N-(beta-Maleimidopropyloxy) succinimide ester (BMPS) (3.7 mMolar) in 1-Methyl-2-pyrrolidinone. After 2 hour mixing at room temperature, the reaction mixture has been washed 6-7 times with 0.1 M PBS buffer containing 0.15 M NaCl, 5 mM EDTA, pH 6.8 through 10 kD cutoff centrifugal filters. Activated protein has been collected in a volume of 0.5 ml in 0.1 M PBS buffer containing 0.15 M NaCl, 5 mM EDTA, pH 6.8 and has been used further for the conjugation. The activated protein has been tested for the total protein content by Lowry method and for maleimide content by Elman assay to determine the maleimide groups per CRM molecule. The data for analysis of activated CRM197 is given in Table 6.

TABLE 6

Activation of CRM197 to generate reactive maleimide group.

| Lot no. of maleimide labelled CRM | Maleimide/ CRM (mol/mol) | % Recovery of CRM (Scale of reaction) |
|---|---|---|
| CRM-001M | 10 | 59 (2.7 mg) |
| CRM-002M | 20 | 32 (24 mg) |
| CRM-003M | 14 | 53 (9 mg) |

TABLE 6-continued

Activation of CRM197 to generate reactive maleimide group.

| Lot no. of maleimide labelled CRM | Maleimide/ CRM (mol/mol) | % Recovery of CRM (Scale of reaction) |
|---|---|---|
| CRM-004M | 10 | 56 (9 mg) |
| CRM-005M | 17 | 42 (10 mg) |
| CRM-006M | 15 | 61 (11 mg) |

EXAMPLE 4

Conjugation of Activated Oligomer (Hib, MenA, MenC, MenY, MenW and MenX) to Activated Protein (TT or CRM) Via Thioether Bond Thiolated oligomer of example 1 in 0.1 M HEPES buffer containing, 0.15 M NaCl, 10 mM EDTA, pH 7.5, at a concentration of 10 mg/ml has been mixed with the freshly prepared ~10 mg/ml of maleimide labelled TT or CRM in 0.1 M PBS, 0.15 M NaCl, 5 mM EDTA, pH 6.8. The reaction mix at a pH of 6.5-7.5 (preferably 7.0) has been kept on gentle stirring for overnight preferably at 2-8° C., the stirring can be carried out at room temperature also. The crude conjugate has been purified by washing 6-7 times with 0.05 M MES buffer containing 0.2 M NaCl pH 6.5 through 50 kD cutoff centrifugal filters to remove unconjugated oligomers and impurities like unreacted hydroxylamine hydrochloride. Final purified conjugates has been filtered through 0.2 µ filters and stored at 2-8° C. till use. The schematic diagram of conjugation is shown in FIG. 2 (2c).

EXAMPLE 5

Physiochemical Analysis of the MenC Oligomer Conjugates Obtained from Example 4

The [MenC]$_4$ & [MenC]$_8$ conjugates have been tested for protein content by Lowry assay using 0.25 mg/ml BSA as a standard and the oligomer content by sialic acid assay using 0.5 mg/ml of N-acetyl neuraminic acid (NANA) as standard. Oligosaccharide protein ratio has been calculated mathematically by wt./wt. basis. The amount of free OS has been evaluated after precipitation with sodium deoxycholate. To 900 µl of conjugate sample (approximately 100 µg OS content), 80 µl of 1% w/v aqueous sodium deoxycholate solution, pH 6.8±0.2 has been added. The reaction mixture has been kept at 2-8° C. for 30 minutes, 50 µl of 1N HCl has been added, and the sample has been centrifuged at 6000×g for 15 minutes. The supernatant has been collected and the free saccharide content estimated by Resorcinol assay (Table 7, 8, 9). HPSEC peak profile of the conjugates have been compared to the HPSEC peak profile of the protein peak, on UV detector to confirm the conversion of all the protein to a conjugate on a TSKgel 4000 PWXL (7.8×300 mm, particle size 7 µm, TOSOH) and TSKgel 3000 PWXL (7.8×300 mm, particle size 7 µm, TOSOH) in series with TSKgel PWXL guard column (6.0×40 mm, TOSOH). The mobile phase is 0.1 M NaNO$_3$, pH 7.2, at the flow rate of 1.0 ml/min in isocratic mode for 30 min. Void and total column volume has been determined with dextran, MW 50, 00,000-400, 00,000 (HI-MEDIA) and deuterium oxide (D$_2$O, Merck), respectively. Protein and conjugate peaks have been detected at 280 nm shown in FIGS. 3a and 3b. Data of characterization of various lots of (MenC)$_4$-TT conjugates, (MenC)$_8$-TT conjugates, (MenC)$_{4\ \&\ 8}$-CRM conjugates is given in Table 7, 8 and 9.

TABLE 7

Characterization of various lots of (MenC)$_4$-TT conjugates

| (MenC)$_4$-TT Conjugate Lot No. | Reaction mixture | | | Free OS | |
|---|---|---|---|---|---|
| | Thiolated (MenC)$_4$ (mg) | Maleimide labelled TT (mg) | OS/TT ratio (w/w) | in purified conjugate (%) | Conjugated OS yield (%) |
| CTM-TT001 | 1.8 | 2.0 | 0.24 | <2.0 | 20 |
| CTM-TT002 | 4.3 | 4.0 | 0.25 | <2.0 | 21 |
| CTM-TT003 | 2.8 | 5 | 0.25 | <2.0 | 32 |
| CTM-TT004 | 4.2 | 8.2 | 0.28 | <2.0 | 47 |
| CTM-TT005 | 2.0 | 3.5 | 0.23 | <2.0 | 38 |
| CTM-TT006 | 3.8 | 12.8 | 0.28 | 5.9 | 39 |
| CTM-TT007 | 3.1 | 11 | 0.20 | <2.0 | 39 |
| CTM-TT008 | 2.9 | 8 | 0.25 | 9.9 | 35 |
| CTM-TT009 | 5.5 | 12 | 0.22 | <2.0 | 34 |
| CTM-TT010 | 6.0 | 8 | 0.23 | <2.0 | 24 |
| CTM-TT011 | 22.7 | 20 | 0.26 | <2.0 | 22 |
| CTM-TT012 | 20.8 | 15 | 0.31 | 2.2 | 20 |

TABLE 8

Characterization of various lots of (MenC)$_8$-TT conjugates

| (MenC)$_8$-TT Conjugate Lot No | Reaction mixture | | | Free OS | |
|---|---|---|---|---|---|
| | Thiolated (MenC)$_8$ (mg) | Maleimide labelled TT (mg) | OS/PR ratio (w/w) | in purified conjugate (%) | Conjugated OS yield (%) |
| COM-TT001 | 6.67 | 10 | 0.22 | <2.0 | 33 |
| COM-TT002 | 5 | 5 | 0.30 | <2.0 | 28 |
| COM-TT003 | 3 | 6.1 | 0.21 | <2.0 | 31 |
| COM-TT004 | 3 | 4 | 0.28 | <2.0 | 29 |
| COM-TT005 | 5.78 | 5.8 | 0.29 | <2.0 | 21 |
| COM-TT006 | 10.8 | 5.0 | 0.45 | <2.0 | 28 |
| COM-TT007 | 10 | 9.0 | 0.33 | <2.0 | 28 |
| COM-TT008 | 6.9 | 7.4 | 0.34 | <2.0 | 37 |
| COM-TT009 | 6.3 | 3.2 | 0.30 | <2.0 | 21 |
| COM-TT010 | 5.9 | 3.6 | 0.37 | <2.0 | 22 |
| COM-TT011 | 16.6 | 16 | 0.42 | 2% | 25 |
| COM-TT012 | 7.3 | 7.5 | 0.41 | <2.0 | 40 |

TABLE 9

Characterization of various lots of (MenC)$_{4\ \&\ 8}$-CRM conjugates

| (MenC)-CRM Conjugate | Reaction mixture | | | Free OS in purified conjugate (%) | Conjugated POS yield (%) |
|---|---|---|---|---|---|
| | Thiolated (Men C) (mg) | Maleimide labelled CRM (mg) | OS/IT ratio (w/w) | | |
| (MenC)$_4$-CRM | 6.8 | 6.7 | 0.26 | <2.0 | 25 |
| (MenC)$_8$-CRM | 8.0 | 4.8 | 0.36 | <2.0 | 20 |

EXAMPLE 6

Physiochemical Analysis of the Hib Conjugates Obtained from Example 4

Figure 3C:
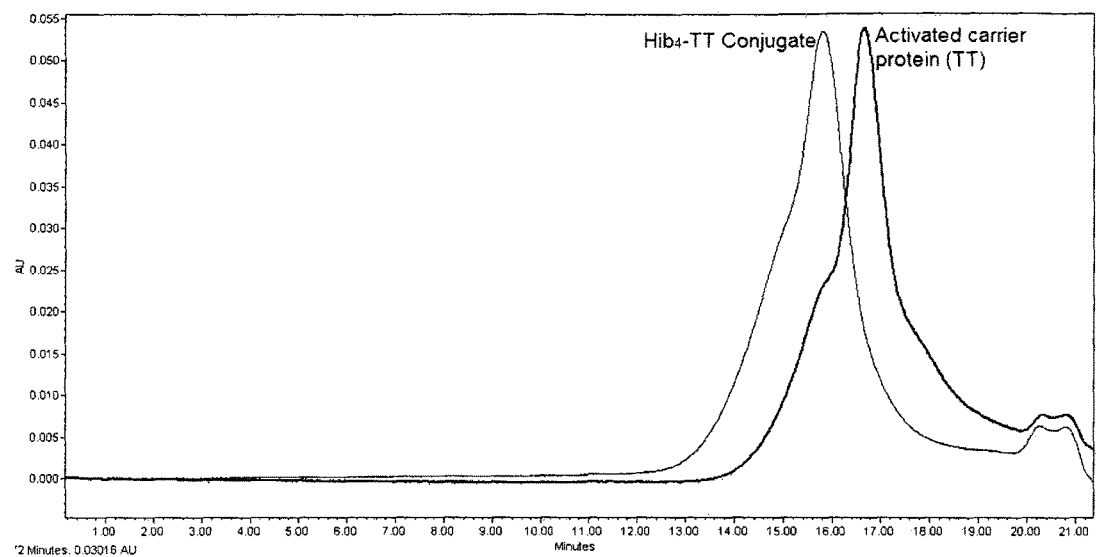
FIG. 3c depicts HP-SEC peak profile of conjugated tetramer Hib compared to the activated protein, as observed on Waters UV/PDA detector.
Figure 4:
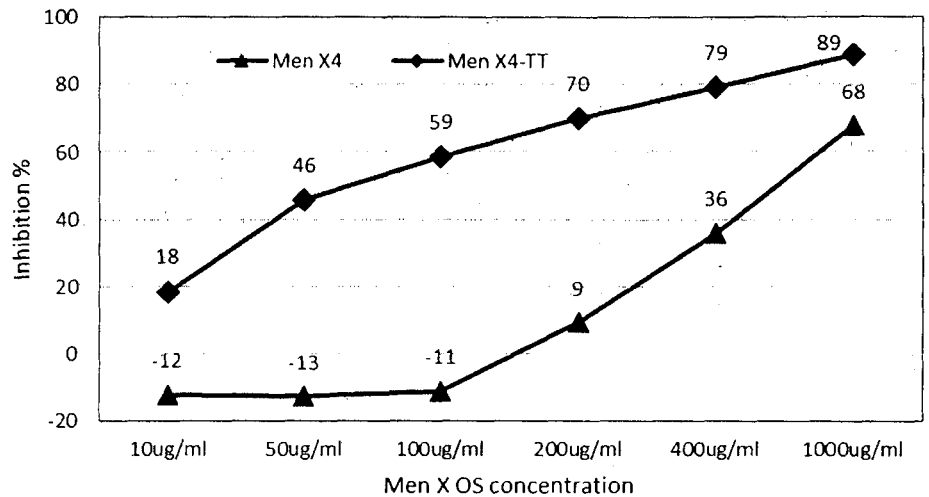
FIG. 4 depicts in vitro antigenic properties of (MenX)$_4$ and (MenX)$_4$-TT conjugate as shown in terms of percent inhibition of antibodies generated against bacterial MenX polysaccharide.

The protein content of the purified conjugate has been determined by Lowry assay using 0.25 mg/ml BSA as a standard, total Hib content by Orcinol assay using 0.2 molar d-Ribose as standard and the ratio of Hib to protein has been calculated mathematically. The free oligosaccharide content has been determined in the supernatant after 1% Deoxycholate (DOC) precipitation as done in previous example. The data of characterization of various lots of (Hib)$_4$-TT conjugates is given in Table 10. (Hib)$_4$-TT conjugates have been analyzed by HP-SEC, in comparison with modified TT used for conjugation as done in previous example to confirm the completion of conversion of a protein (TT or CRM) to a conjugate is shown in FIG. 3c.

TABLE 10

Characterization of various lots of (Hib)$_4$-TT conjugates

| (Hib)$_4$-TT Conjugate Lot No | Reaction mixture | | Hib/ Protein ratio (w/w) | Free Hib in purified conjugate (%) | Conjugated PRP yield (%) |
|---|---|---|---|---|---|
| | Thiolated (Hib)$_4$ (mg) | Maleimide labelled TT (mg) | | | |
| Lot 1 | 1.5 | 3.2 | 0.30 | 6.6 | 55 |
| Lot 2 | 1.6 | 2.4 | 0.46 | 5.2 | 47 |
| Lot 3 | 2.0 | 6.0 | 0.17 | 6.7 | 49 |
| Lot 4 | 3.4 | 5.0 | 0.42 | 6.6 | 62 |
| Lot 5 | 4.0 | 8.0 | 0.31 | 4.3 | 63 |
| Lot 6 | 8.6 | 12.9 | 0.35 | 5.4 | 66 |
| Lot 7 | 8.0 | 14.0 | 0.35 | 2.9 | 59 |

EXAMPLE 7

Physiochemical Analysis of the MenX Conjugates Obtained from Example 4

Figure 3D:
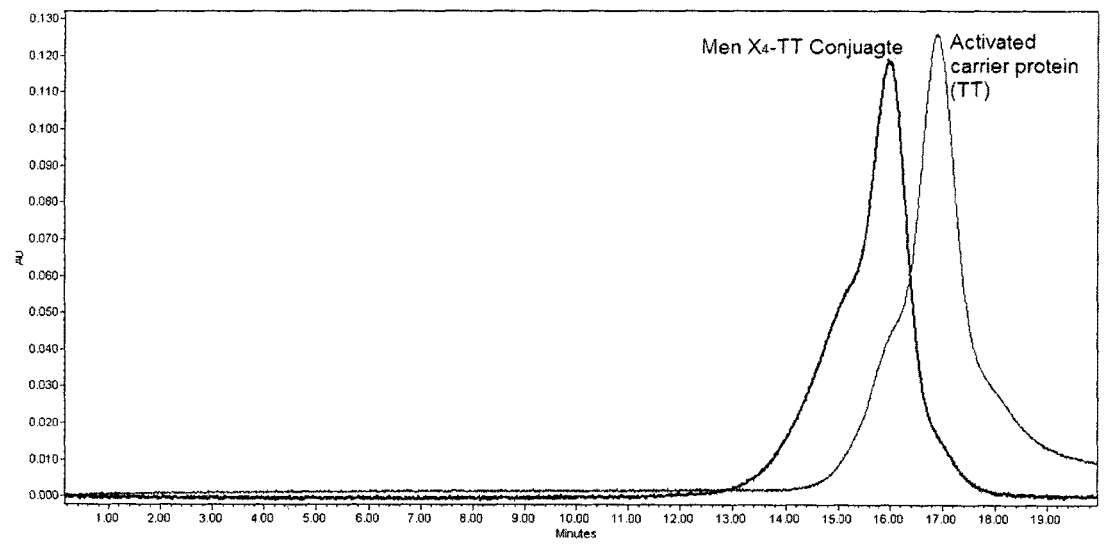
FIG. 3d depicts HP-SEC peak profile of conjugated MenX tetramer compared to the activated protein, as observed on Waters UV/PDA detector.

The [MenX]$_4$ conjugates have been tested for the oligomer content by Chen's assay for phosphorus using 0.2 m Molar phosphorus solution as a standard and for protein content by Lowry assay. The oligosaccharide protein ratio has been calculated mathematically by wt./wt. basis. The amount of free oligosaccharide has been estimated by Resorcinol assay given in Table 11. [MenX]$_4$ conjugates have been analyzed by HPSEC to confirm the complete of conversion of modified carrier protein to the MenX conjugate. The HPSEC peak profile of the conjugates is shown in FIG. 3d.

TABLE 11

Characterization of various lots of (MenX)4-TT conjugates

| (MenX)$_4$-TT Conjugate Lot No. | Reaction Mixture | | | Free OS in purified conjugate (%) | Conjugated OS yield (%) |
|---|---|---|---|---|---|
| | Thiolated (MenX)$_4$ (mg) | Maleimide labelled TT (mg) | OS/PR ratio (w/w) | | |
| βXTM-TT001 | 3.5 | 5.2 | 0.23 | 2.6 | 28 |
| βXTM-TT002 | 5.5 | 8 | 0.24 | <2 | 35 |
| αXTM-TT001 | 11.4 | 13.5 | 0.32 | <2 | 42 |
| αXTM-TT002 | 15.4 | 15.2 | 0.31 | <2 | 22 |
| αXTM-TT003 | 16.1 | 13 | 0.32 | <2 | 28 |

EXAMPLE 8

Physiochemical Analysis of the MenY Conjugates Obtained from Example 4

The [MenY]$_4$ conjugates has been tested for the oligomer content by Sialic acid assay using 0.5 mg/ml of N-acetyl neuraminic acid (NANA) as standard and for protein content by Lowry assay. The oligosaccharide protein ratio has been calculated mathematically by wt./wt. basis. The amount of free oligosaccharide has been estimated by Resorcinol assay given in Table 12. [MenY]$_4$ conjugates have been analyzed by HPSEC to confirm the complete of conversion of modified carrier protein to the [MenY]$_4$ conjugate.

TABLE 12

Characterization of different lots of (MenY)$_4$-TT conjugates

| (MenY)$_4$-TT Conjugate Lot No. | Reaction Mixture | | | Free OS in | |
|---|---|---|---|---|---|
| | Thiolated (MenY)$_4$ (mg) | Maleimide labelled TT (mg) | OS/PR ratio (w/w) | purified conjugate (%) | Conjugated OS yield (%) |
| YTM-TT001 | 5.3 | 7.5 | 0.34 | <2 | 46 |
| YTM-TT002 | 12 | 17 | 0.31 | <2 | 41 |
| YTM-TT003 | 11.8 | 15 | 0.40 | <2 | 48 |

EXAMPLE 9

Physiochemical Analysis of the MenW135 Conjugates Obtained from Example 4

The [MenW]$_4$ conjugates has been tested for the oligomer content by Sialic acid assay using 0.5 mg/ml of N-acetyl neuraminic acid (NANA) as standard and for protein content by Lowry assay. The oligosaccharide protein ratio has been calculated mathematically by wt./wt. basis. The amount of free oligosaccharide has been estimated by Resorcinol assay given in Table 13. [MenW]$_4$ conjugates have been analyzed by HPSEC to confirm the complete of conversion of modified carrier protein to the [MenW]$_4$ conjugates.

TABLE 13

Characterization of various lots of (MenW)$_4$-TT conjugates

| (MenW$_{135}$)$_4$-TT Conjugate Lot No | Reaction Mixture | | | Free OS in purified conjugate (%) | Conjugated OS yield (%) |
|---|---|---|---|---|---|
| | Thiolated (Men W$_{135}$)$_4$ (mg) | Maleimide labelled TT (mg) | OS/TT ratio (w/w) | | |
| WTM-TT001 | 4.15 | 6.25 | 0.25 | <2 | 32 |
| WTM-TT002 | 10 | 13 | 0.29 | <2 | 37 |
| WTM-TT003 | 18.4 | 24 | 0.23 | <2 | 27 |

EXAMPLE 10

Determination of Antigenic Properties of Synthetic MenX-TT Conjugate

The antigenicity of synthetic MenX tetramer-TT conjugate has been compared with MenX tetramer and no-antigen control in a competition enzyme-linked immunosorbent assay (ELISA). In this assay, eight thousand fold diluted rabbit antiserum against Neisseria meningitidis serogroup X (228801; BD) has been incubated for 1 hour at 37° C. with different antigens (synthetic MenX tetramer-TT conjugate and synthetic MenX tetramer) at different concentrations (10, 50, 100, 200, 400, 1000 µg/ml) diluted in phosphate-buffered saline containing 0.1% v/v Brij 35 and 5% FBS; in 96 well micro titer plate (Plate A). A separate plate (plate B) has been coated with a mixture of MenX bacterial polysaccharide and methylated-Human Serum Albumin (m-HSA) and subsequently blocked with 5% FBS after overnight incubation at 2° C.–8° C. To this plate B, antitoxin-antigen mix from plate A has been added and incubated for 1 hour at 37° C. and 1 hour at room temperature. The plate has been washed with phosphate-buffered saline, pH 7.4 containing 0.1% Brij 35. The plate has been incubated for 60 minutes at room temperature with peroxidase labelled anti-rabbit IgG antibodies in PBS, 0.1% Brij 35 and 5% FBS. Plate has been washed again and incubated for 10 minute at room temperature with the 100 µl peroxidase substrate, 3,3',5,5'-tetramethylbenzidine-H$_2$O$_2$ in sodium acetate buffer. The reaction has been stopped by adding 50 µl of 2 M H$_2$SO$_4$. The absorbance (A$_{450}$) has been recorded on an ELISA reader micro plate reader). Results have been plotted as inhibition (%) v/s concentration (µg/ml) and shown in FIG. 4.

EXAMPLE 11

Immunization of Mice with the MenC Oligomeric Conjugates

Groups of 8 female BALB/c mice (5-8 weeks old) have been immunized on days 0, 14 and 28 with 1 µg of Oligomeric MenC conjugates. All immunizations have been performed by administering 200 µl of vaccine dilution via subcutaneous route. Normal saline alone has been used for negative (vehicle) control group, and a multivalent licensed vaccine containing MenC bacterial polysaccharide conjugate has been used for immunizing positive control group. Sera have been collected at days 14, 28 and 35. Specific anti-OS IgG antibody titers have been estimated by indirect ELISA. Animals have been dosed with different Synthetic MenC conjugates as per table 14.

TABLE 14

Different (MenC)$_4$ Conjugate formulations to study the immunogenicity in mouse model

| Sr. No. | Antigen type | Dose |
|---|---|---|
| Formulation F1 | Negative/Vehicle Control | — |
| Formulation F2 | Licensed vaccine equivalent to 1 µg conjugated MenC conjugate (Positive Control) | 1 µg |
| Formulation F3 | (MenC)$_4$-TT Conjugate | 1 µg |
| Formulation F4 | (MenC)$_4$-CRM Conjugate | 1 µg |
| Formulation F5 | (MenC)$_8$-TT Conjugate | 1 µg |
| Formulation F6 | (MenC)$_8$-CRM Conjugate | 1 µg |

EXAMPLE 12

Determination of Antigenic Properties of Synthetic MenC-TT & Synthetic MenC-CRM Conjugates by IgG ELISA Ninety six-well plates (Nunc Maxisorp) have been coated with MenC PS by adding 100 µl per well mixture of a 5 µg/ml PS and m-HSA in PBS buffer, pH 7.4. Plates have been incubated overnight at 4° C., and then washed three times with PBS buffer (0.1% Brij 35 in PBS, pH 7.4) and blocked with 200 µl per well of 5% FBS solution in PBS buffer (0.1% Brij 35 in PBS, pH 7.4) for 1 hour at 37° C. Each incubation step has been followed by three PBS buffer wash. Reference and test sera samples have been diluted in PBS buffer (0.1% Brij 35, 5% FBS in PBS, pH 7.4), transferred into coated-blocked plates (200 µl), and serially twofold diluted followed by overnight incubation at 4° C. Then 100 µl per well of 1:1000 diluted peroxidase conjugated anti-mouse IgG have been added and left for 1 hour at 25° C. 100 μl per well of substrate, 3, 3', 5, 5'-tetramethyl-benzidine-$H_2O_2$ has been added for color development. After 10 minutes of development at 25° C., reaction has been stopped by adding 50 μl of 2 M $H_2SO_4$, and OD has been measured at 450 nm on Micro plate reader. Anti-MenC polysaccharide IgG concentrations (in terms of ELISA Units/ml) for each formulation have been evaluated using Combistat software and the geometric mean concentrations (IgG GMC) have been shown in FIG. 5a.

EXAMPLE 13

Serum Bactericidal Assay (SBA) for the Synthetic (MenC)$_4$-TT Conjugates & (MenC)$_8$-TT Conjugates

*N. meningitidis* serogroup C bacterial stock (ATCC® 13102™) has been grown overnight on sheep blood agar plate at 37° C. with 5% $CO_2$. Isolated colonies have been picked and incubated for 4 h on the surface of another sheep blood agar plate at 37° C. with 5% $CO_2$. One or two loopful bacteria have been suspended in 5 ml of assay buffer (5% bovine serum albumin in Hank's balanced salt solution without calcium and magnesium), and the optical density ($OD_{650}$) of the suspension has been adjusted to 0.1 which has been further diluted using assay buffer to achieve the working dilution of 6 to $10 \times 10^4$ colony-forming units per ml. Quality control (QC) sera and test sera samples have been heat inactivated for 30 min at 56° C. In micro well plate, 20 μl of serial two fold dilutions of test serum has been mixed with 10 μl of bacteria at the working dilution and 10 μl of baby rabbit complement (Pel-Freez). For negative controls bacteria have been incubated, in a separate well, with baby rabbit complement and without the test serum and with test serum and heat-inactivated baby rabbit complement. The well contents have been mixed by gently tapping the assay plate and incubated the plates for 1 hour at 37° C. with 5% $CO_2$. Ten μL sample from each well plated on blood agar plate by streak plate method. The blood agar plates have been incubated overnight at 37° C. with 5% $CO_2$ and colonies have been counted. The highest serum dilution showing ≥50% decrease in colony-forming units per ml after incubation of bacteria with reaction mixture, as compared to respective active complement control was considered as the SBA titer.

Figure 5A:
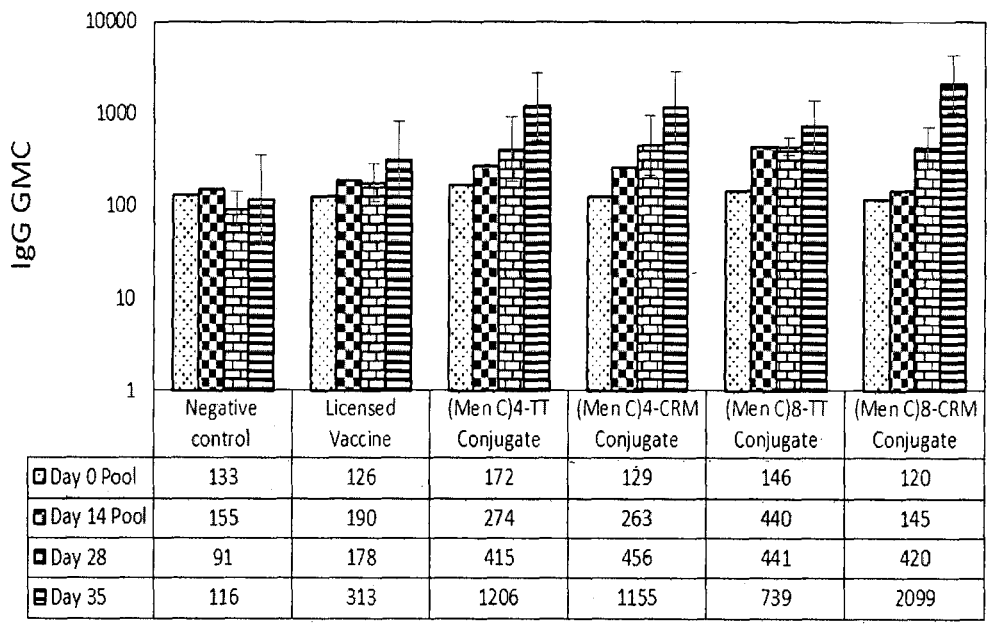
FIG. 5a depicts immunological response with respect to anti-MenC serum IgG concentrations in Swiss albino mice post 1, 2&3 dose of synthetic MenC conjugates as estimated by ELISA.
Figure 5B:
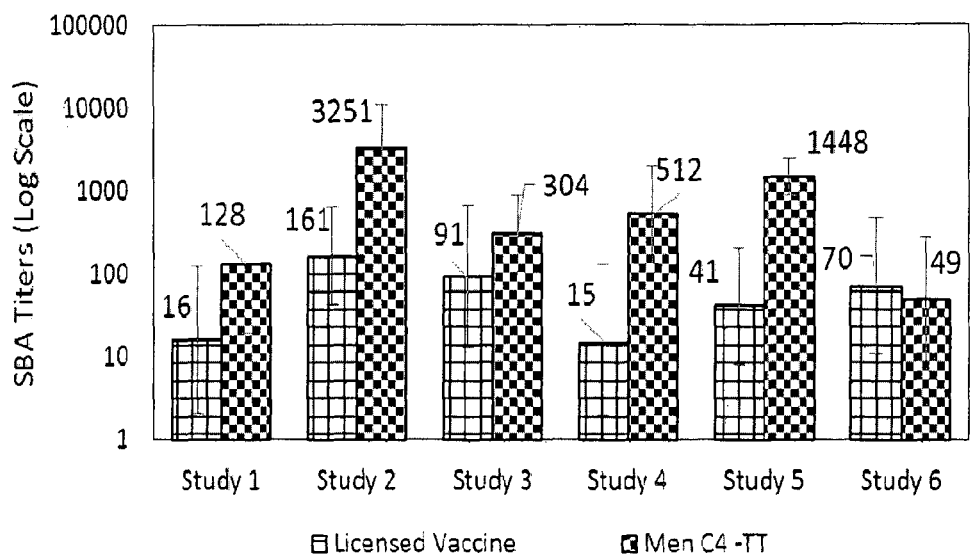
FIG. 5b depicts post 3 dose immunological response with respect to anti-MenC serum bactericidal assay titers for (MenC)$_4$-TT conjugates.
Figure 5C:
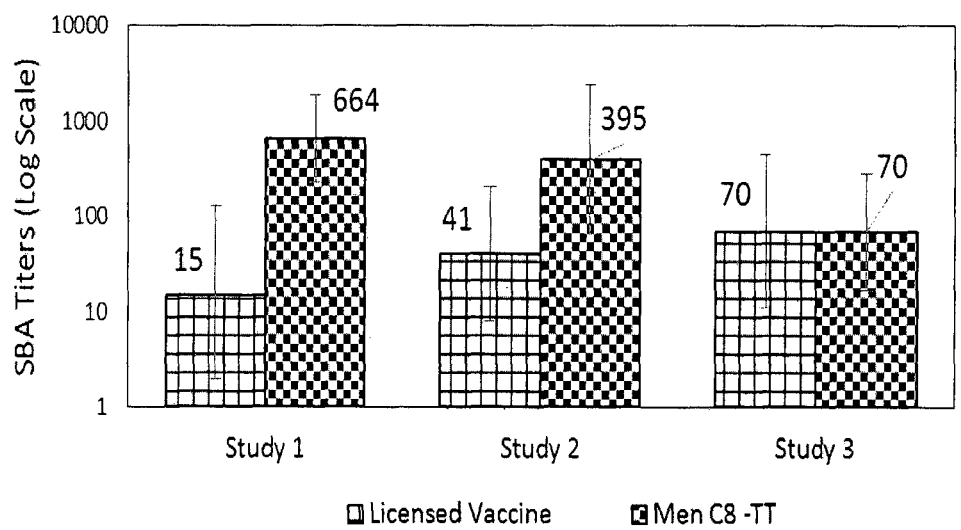
FIG. 5c depicts post 3 dose immunological response with respect to anti-MenC serum bactericidal assay titers for (MenC)$_8$-TT conjugates

Six different studies have been considered to evaluate the SBA titers for Men C tetramer in comparison to Licensed vaccine and results are depicted in FIG. 5b. Three studies have been considered for the SBA titer evaluation of Men C octamer and results are depicted in FIG. 5c.

The immunological and serum bactericidal assay reveals that the OS-PR conjugates of the present invention result in higher total IgG antibody titers. The OS-PR conjugates after 3 doses at 1 μg dose display more than 4 fold higher and upto 18 fold higher IgG titers than the pre-immunization titers for meningitis C oligosaccharide conjugate. The total IgG titers are comparable or higher than the licensed vaccine titers for MenC.

The functional antibody titers (also referred to as SBA titers) are always more than 4 fold higher than the pre-immunization SBA titers for MenC protein conjugates and are comparable or higher than the licensed vaccine titers.

EXAMPLE 14

Immunization of Mice with (MenX)$_4$-TT Conjugate and IgG Determination by ELISA Groups of 8 female BALB/c mice (5-8 weeks old) have been immunized on days 0, 14 and 28 with 1 and 0.1 μg (200 μl) of (MenX)$_4$-TT conjugate formulated in normal saline via subcutaneous route. Normal saline alone has been used for negative control group. Sera have been collected at days 14, 28 and 35. As there is no commercial vaccine available for the group MenX, the titers have been compared to the negative control. Study included two different doses (1 & 0.1 μg) and evaluation of two different lots of αXTM-TT and one lot of βXTM-TT conjugate. Different (MenX)$_4$ Conjugate formulations were taken to study its immunogenicity in mouse model as per FIG. 5d.

Figure 5D:
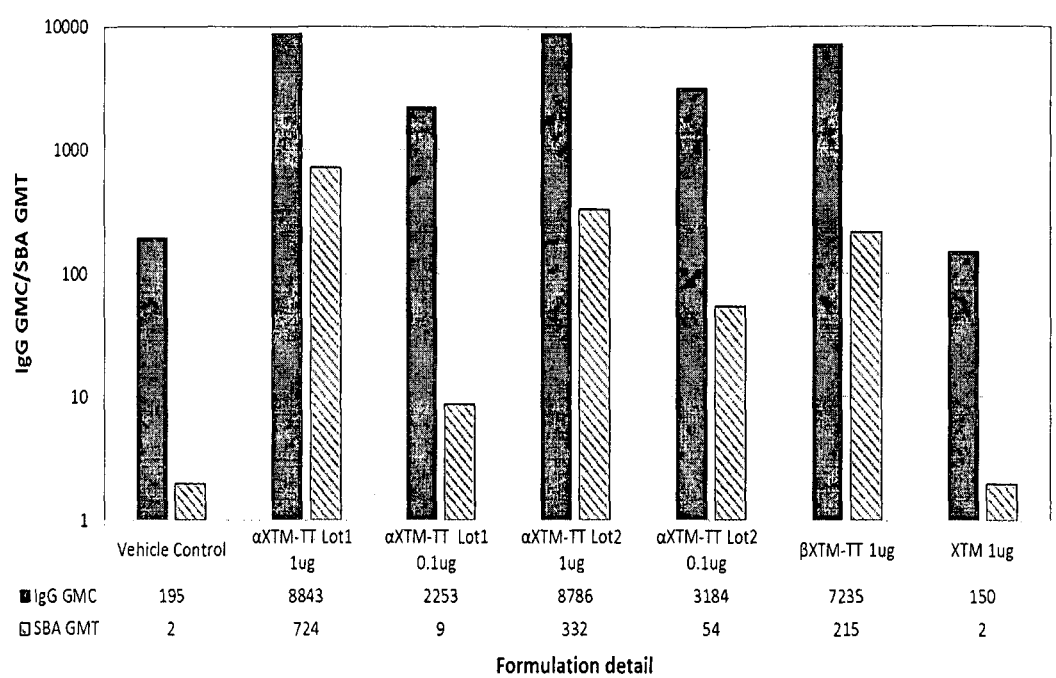
FIG. 5d depicts immunological responses with respect to anti-MenX IgG response as estimated by ELISA and Serum bactericidal titers post 3 doses of synthetic (MenX)$_4$-TT conjugates in Swiss albino mice.

Specific anti-OS IgG antibody titers have been estimated by ELISA. Ninety six-well plates (Nunc Maxisorp) have been coated with bacterial MenX PS by adding 100 μl per well mixture of a 5 μg/ml PS and m-HSA in PBS buffer, pH 7.4. Plates have been incubated overnight at 4° C., and then washed three times with PBS buffer (0.1% Brij 35 in PBS, pH 7.4) and blocked with 200 μl per well of 5% FBS solution in PBS buffer (0.1% Brij 35 in PBS, pH 7.4) for 1 hour at 37° C. Each incubation step has been followed by three PBS buffer wash. All the sera samples have been diluted in PBS buffer (0.1% Brij 35, 5% FBS in PBS, pH 7.4), transferred into coated-blocked plates (200 μl), and serially twofold diluted followed by overnight incubation at 4° C. Then 100 μl per well of 1:1000 diluted peroxidase conjugated anti-mouse IgG were added and left for 1 hour at 25° C. 100 μl per well of substrate, 3, 3', 5, 5'-tetramethyl-benzidine-$H_2O_2$ was added for color development. After 10 minutes of development at 25° C., reaction has been stopped by adding 50 μl of 2 M $H_2SO_4$, and OD has been measured at 450 nm on Micro plate reader. IgG GMCs for each formulation has been evaluated using Combistat software as shown in FIG. 5d.

EXAMPLE 15

Serum Bactericidal Assay (SBA) for the Synthetic (MenX)$_4$-TT Conjugates

*N. meningitidis* serogroup X bacterial stock (ATCC® 35560) has been grown overnight on sheep blood agar plate at 37° C. with 5% $CO_2$. Isolated colonies have been picked and incubated for 4 h on the surface of another sheep blood agar plate at 37° C. with 5% $CO_2$. One or two loopful bacteria have been suspended in 5 ml of assay buffer (5% bovine serum albumin in Hank's balanced salt solution with calcium and magnesium), and the optical density (OD650) of the suspension has been adjusted to 0.1 which has been further diluted using assay buffer to the working dilution of 6 to $10 \times 10^4$ colony-forming units per ml. Quality control (QC) sera and test sera samples have been heat inactivated for 30 min at 56° C. In micro well plate, 20 μl of serial two fold dilutions of test serum mixed with 10 μl of bacteria at the working dilution and 10 μl of baby rabbit complement (Pel-Freez). For negative controls bacteria have been incubated, in a separate well, with baby rabbit complement and without the test serum and with test serum and heat-inactivated baby rabbit complement. The well contents have been mixed by gently tapping the assay plate and incubated the plates for 1 hour at 37° C. with 5% $CO_2$. Ten μL sample from each well plated on blood agar plate by streak plate method. The blood agar plates have been incubated overnight at 37° C. with 5% $CO_2$ and colonies have been counted. The highest serum dilution showing ≥50% decrease in colony-forming units per ml after incubation of bacteria with reaction mixture, as compared to respective active complement control is considered as the SBA titer.

Three different MenX conjugates have been evaluated against the negative (vehicle) control sera and the unconjugated MenX tetramer and the results are presented as per FIG. 5d. The total IgG and SBA titers for MenX-TT conjugates are at least 4 fold higher than the negative (vehicle) control and are upto 45 fold higher in terms of total IgG and upto 350 fold higher SBA titers than the negative (vehicle) control.

We claim:

1. A process of conjugation to obtain synthetic oligosaccharide-protein conjugates comprising the steps of:
   (a) reacting a synthetic oligosaccharide having at least one terminal amine linker with a reagent having at least one reactive thiol functional group to obtain an activated synthetic oligosaccharide;
   (b) reacting a carrier protein with at least one aliphatic hetero bifunctional crosslinker to obtain an activated carrier protein having reactive maleimide functional group;
   (c) carrying out a conjugation reaction of said activated synthetic oligosaccharide of step (a) with said activated carrier protein of step (b) to obtain a synthetic oligosaccharide-protein conjugate (OS-PR) having thioether linkage;
   wherein
   said synthetic oligosaccharide of step (a) mimics the chemical composition of the natural polysaccharides of gram negative bacteria selected from *Neisseria meningitidis* and *Haemophilus influenza;*
   said step of carrying out the conjugation reaction is completed in 14 hours to 22 hours; and
   said OS-PR conjugate is in a purified form;
   thereby yielding OS-PR conjugates for the preparation of synthetic oligosaccharide based conjugates for use in vaccines or as diagnostic tools.

2. The process of conjugation as claimed in claim 1 wherein said synthetic oligosaccharide comprises:
   at least one in-built terminal amino linker,
   four to eight repeating monomeric units of polysaccharides.

3. The process of conjugation as claimed in claim 2 wherein said *Neisseria meningitidis* comprises of serogroups A, C, Y, W135, X and said *Haemophilus influenzae* comprises of type b.

4. The process of conjugation as claimed in claim 1 wherein said carrier protein is obtained from gram positive bacteria selected from *Clostridium tetani* (tetanus toxoid), *Corynebacterium diphtheriae* (CRM197) or recombinant versions thereof.

5. The process of conjugation as claimed in claim 1 wherein said activated synthetic oligosaccharide is obtained by the steps of:
   (a) reacting said synthetic oligosaccharide having at least one terminal amine linker with at least one sulfhydrilating agent to predetermined conditions to obtain a sulfhydrilated oligosaccharide;
   (b) subjecting said sulfhydrilated oligosaccharide of step (a) to gel filtration chromatography to remove unreacted sulfhydrilating agent;
   (c) reacting said sulfhydrilated oligosaccharide obtained from step (b) with at least one nucleophile to obtain said activated synthetic oligosaccharide leading to recovery of said activated synthetic oligosaccharide with a yield in the range of 40% to 90%;
   wherein said predetermined conditions are addition of 2-5× molar excess of said sulfhydrilating agent at a pH of 6.0-8.0.

6. The process of conjugation as claimed in claim 5 wherein said sulfhydrilating agent is a chemical sulfhydrilating agent to facilitate conversion of terminal amino linker to sulfhydryl group.

7. The process of conjugation as claimed in claim 5 wherein said nucleophile is a reducing agent that facilitates conversion of sulfhydryl group to reactive thiol group.

8. The process of conjugation as claimed in claim 1 wherein said aliphatic heterobifunctional crosslinker is a chemical crosslinker to generate reactive maleimide functional group.

9. The process of conjugation as claimed in claim 1 wherein said OS-PR conjugate yield is in the range of 21% to 48% for Meningococcal conjugates selected from MenX, MenC, MenW135, and MenY conjugates; and in the range of 45% to 65% for Hib conjugates.

10. The process of conjugation as claimed in claim 1 wherein said process results in higher total IgG antibody titers and SBA titers at 1 µg dose.

11. The process of conjugation as claimed in claim 1 wherein said OS-PR conjugate displays high immunogenicity and antigenicity, wherein
    said high immunogenicity is displayed by total IgG titers being in the range of 4 fold to 18 fold higher than the pre-immunization titers for serogroup C oligosaccharide conjugates, and
    said high antigenicity is displayed by SBA titers being in the range of at least 4 fold higher than the pre-immunization SBA titers for serogroup C oligosaccharide conjugates.

12. The process of conjugation as claimed in claim 1 wherein said process is carried out in the absence of nitrogen purging.

13. A synthetic OS-PR conjugate obtained from the process as claimed in claim 1 wherein said synthetic OS-PR conjugate elicits a specific and homogenous immune response and is capable of being used in the preparation of synthetic conjugate vaccines, either in single or as combination vaccines and also as diagnostic tool.

14. The synthetic OS-PR conjugate as claimed in claim 13 wherein said conjugate has an OS/PR ratio in the range of 0.17 to 0.5 (w/w).

15. The process of conjugation as claimed in claim 1 wherein said high immunogenicity and high antigenicity is displayed by total IgG titers and SBA titers for MenX oligomer-TT conjugates being in the range of 4 fold higher than the negative (vehicle) control and upto 45 fold higher in terms of total IgG and upto 350 fold higher SBA titers than the negative (vehicle) control.

16. The process of conjugation as claimed in claim 5 wherein wherein said predetermined conditions are addition of 2.5× molar excess of said sulfhydrilating agent at a pH of 7.5.

17. The process of conjugation as claimed in claim 6 wherein said sulfhydrilating agent is N-succinimidyle S-acetylthio acetate (SATA).

18. The process of conjugation as claimed in claim 7 wherein said reducing agent is hydroxyl amine hydrochloride.

19. The process of conjugation as claimed in claim 8 wherein said aliphatic heterobifunctional crosslinker is N-(beta-maleimidopropyloxy) succinimide ester (BMPS).

20. The process of conjugation as claimed in claim 9 wherein said OS-PR conjugate yield for said Meningococcal conjugates is in the range of 25% to 30%; and in the range of 50% to 60% for said Hib conjugates.

21. The synthetic OS-PR conjugate as claimed in claim 14 wherein said conjugate has an OS/PR ratio in the range of 0.2 to 0.4 (w/w).

\* \* \* \* \*